United States Patent
Saur (10) Patent No.: US 11,937,986 B2
(45) Date of Patent: Mar. 26, 2024

(54) METHOD FOR ACQUIRING ANNOTATED DATA WITH THE AID OF SURGICAL MICROSCOPY SYSTEMS

(71) Applicant: Carl Zeiss Meditec AG, Jena (DE)

(72) Inventor: Stefan Saur, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 326 days.

(21) Appl. No.: 17/241,978

(22) Filed: Apr. 27, 2021

(65) Prior Publication Data
US 2021/0335482 A1 Oct. 28, 2021

(30) Foreign Application Priority Data
Apr. 28, 2020 (DE) .......................... 102020111563.6

(51) Int. Cl.
*G06T 7/00* (2017.01)
*A61B 90/20* (2016.01)
(Continued)

(52) U.S. Cl.
CPC .............. *A61B 90/20* (2016.02); *G06F 18/24* (2023.01); *G06T 7/0014* (2013.01); *G06V 10/764* (2022.01); *G06V 10/774* (2022.01); *G06V 10/7784* (2022.01); *G16H 20/40* (2018.01); *G16H 30/20* (2018.01); *G16H 30/40* (2018.01);
(Continued)

(58) Field of Classification Search
CPC ........ A61B 90/20; G16H 20/40; G16H 30/20; G16H 30/40; G06V 10/7784; G06V 10/774; G06V 10/764; G06V 2201/03; G06F 18/24; G06T 7/0014; G06T 2207/10056; G06T 2207/30004; G06T 2207/30168
See application file for complete search history.

(56) References Cited

U.S. PATENT DOCUMENTS 10,474,917 B2 * 11/2019 Sharma ................. G16H 30/40
10,762,605 B2 * 9/2020 Chui ..................... G06V 20/64
(Continued)

FOREIGN PATENT DOCUMENTS

DE      102019113493 A1   11/2019
WO        2018152248 A1    8/2018

OTHER PUBLICATIONS

German Office Action, with translation thereof, for corresponding DE application No. 10 2020 111 563.6 dated Jan. 28, 2021, 20 pages.

*Primary Examiner* — Shefali D Goradia
(74) *Attorney, Agent, or Firm* — Honigman LLP; Brett A. Krueger (57) ABSTRACT

A method for acquiring annotated data with the aid of surgical microscopy systems comprises obtaining desired criteria which are intended to be satisfied by desired data to be annotated, and storing the set of desired criteria in a plurality of surgical microscopy systems. In each surgical microscopy system, images are then recorded and current criteria which correspond to the recorded images are determined. The current criteria are compared with the desired criteria. If the desired criteria sufficiently correspond to the current criteria, a confirmation is requested from a user as to whether said user would like to annotate data. If the user provides the confirmation, annotations for images are received from the user and stored together with the images.

16 Claims, 5 Drawing Sheets

(51) Int. Cl.
  *G06F 18/24*   (2023.01)
  *G06V 10/764*  (2022.01)
  *G06V 10/774*  (2022.01)
  *G06V 10/778*  (2022.01)
  *G16H 20/40*   (2018.01)
  *G16H 30/20*   (2018.01)
  *G16H 30/40*   (2018.01)

(52) U.S. Cl.
  CPC .............. *G06T 2207/10056* (2013.01); *G06T 2207/30004* (2013.01); *G06T 2207/30168* (2013.01); *G06V 2201/03* (2022.01)

(56) References Cited

U.S. PATENT DOCUMENTS

| | | |
|---|---|---|
| 11,023,785 B2 * | 6/2021 | Kartoun .............. G06F 18/2433 |
| 2014/0160264 A1 * | 6/2014 | Taylor .................... A61F 9/008 |
| | | 348/79 |
| 2017/0103512 A1 * | 4/2017 | Mailhe ................. G06V 10/993 |
| 2018/0144466 A1 | 5/2018 | Hsieh et al. |
| 2019/0350564 A1 | 11/2019 | Gajdos et al. |
| 2020/0129263 A1 | 4/2020 | Izadyyazdanabadi et al. |

* cited by examiner

METHOD FOR ACQUIRING ANNOTATED DATA WITH THE AID OF SURGICAL MICROSCOPY SYSTEMS

CROSS-REFERENCE TO RELATED APPLICATIONS

This application claims priority of German Patent Application No. 10 2020 111 563.6 filed on Apr. 28, 2020, the contents of which are incorporated herein.

TECHNICAL FIELD

The present disclosure relates to methods for acquiring annotated data with the aid of surgical microscopy systems.

The present application is related to the further German patent application 10 2020 111 584.9 filed on Apr. 28, 2020, which is entitled "Method for acquiring data with the aid of surgical microscopy systems" and is incorporated by reference in its entirety in the present application.

BACKGROUND

In the field of medicine, it is necessary to take a variety of decisions based on the analysis of data. By way of example, said decisions may comprise diagnoses regarding the presence or absence of a state on the basis of chemical or physical analyses, for example, decisions about treatments to be carried out or use of aids on the basis of diagnoses and other information. Machine learning techniques are increasingly being used to support such decisions. Machine learning techniques comprise the use of instruments such as of a classifier, for example, which, on the basis of features that have been input, can effect an assignment of the features that have been input to classes of a feature space. Such classifiers are trained using realistic data, and so the quality of the classifications effected by the classifier improves as the amount of realistic data available and the quality of the realistic data available increase. Accordingly, it is desirable to obtain data for training machine learning instruments in large amounts and with good quality.

However, obtaining large amounts of high-quality data is not easy, since the existing processes in the medical field are primarily designed for optimum treatment of patients and reduction of costs. Acquiring data that form the basis for developing machine learning instruments can be effected in parallel with the progression of the existing medical processes only with additional outlay and can even disturb these processes. Acquiring data suitable for training machine learning instruments thus intrinsically proves to be a technical problem.

Accordingly, it is an object of the present disclosure to propose a method for acquiring data in the medical field which are suitable for training a machine learning instrument, such as a classifier, for instance.

SUMMARY

The disclosure therefore proposes a method for acquiring an annotated data with the aid of surgical microscopy systems. Large numbers of surgical microscopy systems are installed in hospitals and doctors' practices and are used for treating patients. In this case, the surgical microscopy systems in the course of their use on patients can continuously record images of the regions of the patients in need of treatment. Furthermore, sequences of images recorded by the surgical microscopy systems also document measures actually performed on the treated patient. The images recorded by a surgical microscopy system are thus data having a high relevance to training a machine learning instrument. However, the images alone are not always sufficient for this purpose, since the training of specific machine learning instruments requires annotated data. Annotations with respect to data present are additional information with respect to the data or about the data, this additional information being added to the data present by an expert. Data provided with annotations are also called "labelled data".

In accordance with exemplary embodiments, the method comprises obtaining at least one set of desired criteria which are intended to be satisfied by desired data to be annotated, and storing the set of desired criteria in a plurality of surgical microscopy systems. In this case, the plurality of surgical microscopy systems can comprise for example the surgical microscopy systems which are installed for example in a hospital or in a group of hospitals. Furthermore, the plurality of surgical microscopy systems can comprise systems of a manufacturer of surgical microscopy systems which are installed at different locations. The surgical microscopy systems in which at least one set of desired criteria is stored can then be used for acquiring annotated data. Since currently a large amount of surgical microscopy systems have already been installed, a potentially large source of data suitable for training machine learning instruments in the medical field is available in this way.

In accordance with exemplary embodiments, the following method is carried out by each surgical microscopy system of the plurality of surgical microscopy systems: Images are recorded by the microscope of the surgical microscopy system, and the recorded images are taken as a basis for determining a set of current criteria which correspond to the recorded images. This determination can be effected automatically by means of software-aided analysis of the recorded images. By way of example, in this case it is possible to determine that a cataract operation or a brain operation is currently being carried out by means of the surgical microscopy system. By way of example, it is also possible to determine whether fluorescent substances are used. Machine learning instruments, such as classifiers trained on the basis of training data, for instance, can likewise be used in the automatic determination of the current criteria. Besides the analysis of the recorded images themselves, it is also possible to use other sources of information in order to determine current criteria which correspond to the recorded images. By way of example, data which correspond to the subsequently recorded images can be stored in the surgical microscopy system prior to the use thereof for a specific purpose. Examples of this are the type of a medical intervention, an age, a sex and a state of health of a patient on whom the medical intervention is performed using the relevant surgical microscopy system.

The method can then furthermore comprise comparing the set of current criteria with the stored sets of desired criteria. If a set of the desired criteria sufficiently corresponds to the set of current criteria, a confirmation can then be requested from a user of the surgical microscopy system as to whether or not said user would like to annotate data. This means that users of the surgical microscopy system are not asked for confirmations as to whether or not they would like to annotate data every time they use the surgical microscopy system, since the process of requesting such confirmations might already disturb the users. Such a request for a confirmation from the user is demanded only in cases in which the desired criteria sufficiently correspond to the set of current criteria. If the user would still like to continue using the surgical microscopy system without being disturbed and would not like to annotate data, said user can react to the request for the confirmation by declining it. In this case, the method in accordance with the embodiment explained implements no further steps suitable for disturbing the user in the course of further work with the surgical microscopy system. However, if the user feels able additionally to annotate data besides the customary and necessary use of the surgical microscopy system, said user can provide the confirmation desired by the method. The surgical microscopy system is then ready to receive at least one annotation for at least one image from the user and to store the at least one image together with the at least one annotation. In order to receive the at least one annotation, the method can provide the user with the necessary means, such as input masks of a graphical user interface, for example. This can either be done in the direct temporal context, that is to say immediately, which may possibly distract the user somewhat from his/her work, but it can also be done at a later time, such as, for instance, after the conclusion of the medical intervention carried out.

A method is thus provided which can acquire annotated data on the basis of a potentially large number of installed surgical microscopy systems, wherein the users' usual, customary work with the surgical microscopy systems is only slightly disturbed since it is only in selected cases that the users are actually requested for a confirmation of their wanting to annotate data, the users also being able to decline this.

In accordance with exemplary embodiments, the desired criteria represent a type of a medical intervention, an age, a sex and/or a state of health of a patient on whom the medical intervention is performed. By way of example, the patient's state of health can concern the presence of a specific symptom, such as, for example, the presence of a cataract, a detached retina or a specific tumour, which are intended to be treated with the aid of the surgical microscopy system. The desired criteria can furthermore represent a quality of tissue imaged in the images, such as, for example, healthy tissue, tumour tissue, fluorescent-substance-containing tissue and the like. The desired criteria can furthermore represent a characteristic of the user of the surgical microscopy system, such as, for instance, the user's age, the user's experience for a specific type of medical intervention and the like. Furthermore, the desired criteria can represent a location at which the surgical microscopy system is situated. The desired criteria can furthermore concern for example a use history of the surgical microscopy system, such as, for example, the information that a relevant surgical microscopy system is principally used for fluorescence examinations.

In accordance with exemplary embodiments, determining the set of criteria which correspond to the recorded images comprises requesting at least one criterion from the user, and/or obtaining at least one criterion from an information management system of a hospital in which the surgical microscopy system is situated, and/or of a company which manufactured the surgical microscopy system, and determining at least one criterion on the basis of the recorded images. Such an information management system can be a central database with localized data memories which is arranged at the institution that operates the information management system, such as a hospital or manufacturer, for instance. However, such an information management system can also be a distributed database system which stores associated data at different locations, wherein specific data can be stored only to a lesser extent at specific locations in order to comply with possible data protection rules.

In accordance with exemplary embodiments, the set of the desired criteria sufficiently corresponds to the set of current criteria if an intersection of the criteria has a number of criteria that satisfies a predetermined relation with respect to a number of the criteria of the set of desired criteria. By way of example, sufficient correspondence can be present in this case if the number of criteria in the intersection is greater than two or greater than ten or if the number of criteria in the intersection is greater than half or greater than three quarters of the number of criteria of the set of desired criteria. In accordance with exemplary embodiments, the annotation comprises a designation indicating a quality of tissue imaged in the images, and/or comprises at least one graphical marking within the recorded image. In this regard, for example, the designation can read "tumour tissue" if the user would like to indicate a designation as annotation. If the user would like to indicate a graphical marking as annotation, this can be for example a circle enclosing the designated tissue, or an arrow directed at the designated tissue. The designation can be input by the user for example via a keyboard or by voice input. The graphical marking can be input by the user for example by operating a graphical user interface using a mouse or the like.

In accordance with exemplary embodiments, storing the at least one image together with the at least one annotation comprises storing the image and the annotation in a database shared by all the surgical microscopy systems. It is thereby possible, in a simple manner, to collect the annotated data and to use them to create a machine learning instrument.

In accordance with exemplary embodiments, the method therefore furthermore comprises analysing the images stored together with the annotations, wherein the analysing comprises in particular generating a classifier with which at least one criterion of the set of desired criteria is determinable on the basis of an image which is recorded by a surgical microscope. In this case, the surgical microscope used to record the recorded image can be different from the plurality of surgical microscopy systems which were used for acquiring the annotated data.

DESCRIPTION OF DRAWINGS

Embodiments of the disclosure are explained below with reference to figures, in which.

DETAILED DESCRIPTION

Figure 1:
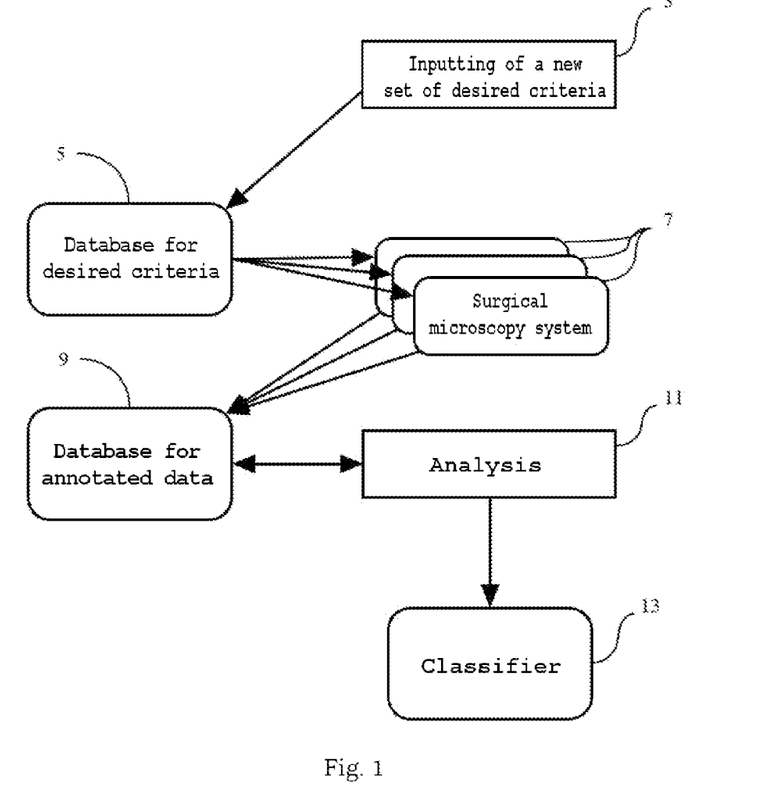
FIG. 1 shows a flow diagram of a method for acquiring annotated data in accordance with one embodiment.

FIG. 1 is a diagram for elucidating a method for acquiring annotated data with the aid of surgical microscopy systems. In a step 3, a set of desired criteria is obtained by a user who desires annotated data inputting this set of desired criteria via a suitable user interface. In this case, inputting the set of the desired criteria can also comprise a selection from predetermined criteria. The desired criteria can specify for example the type of the desired data. Examples thereof are "image", "video", "fluorescence", "OCT" and the like. The desired criteria can furthermore specify for example the type of the desired annotations. Examples thereof are "tissue designation", "contour line", "arrow marking" and the like. The desired criteria can furthermore specify for example the type of the desired medical intervention. Examples thereof are "neuro", "vascular", "aneurism", "tumour", "glioblastoma", "meningioma", "spinal column", "eye", "anterior chamber of the eye", "posterior chamber of the eye", "cataract", "retina", "membrane peeling" and the like. The desired criteria can furthermore specify for example the desired phase of a medical intervention. The desired criteria can furthermore specify a desired characteristic of the patient. Examples thereof are "male", "female", "20-30 years old", "25-35 years old", "pre-existing disease X" and the like. The desired criteria can furthermore specify a desired characteristic of the user. Examples thereof are "5-10 years of professional experience" and the like. The desired criteria can furthermore specify a desired state of the surgical microscopy system. Examples thereof are "microscope is in the fluorescence mode", "set magnification is greater than 10 fold" and the like.

The set of desired criteria that has been input in step 3 is subsequently stored in a database 5 for desired criteria. Further sets of desired criteria may also already have been stored or will subsequently be stored in said database 5 for desired criteria. The sets of desired criteria that have been stored in the database 5 for desired criteria are communicated to a plurality of surgical microscopy systems 7. This communication can be effected for example in such a way that each surgical microscopy system 7 obtains a copy of the database 5 for desired criteria. However, it is also possible that each of the surgical microscopy systems 7 as necessary can access the database 5 for desired criteria in order to obtain the sets of desired criteria.

The surgical microscopy systems 7 typically comprise a surgical microscope 73 with the microscopy optics and with sensors, such as cameras or OCT scanners, for instance, a stand for mounting the surgical microscope 73 and a control system for controlling the surgical microscope 73 and for providing functionalities. The control system can provide user interfaces, databases and remote data connections, inter alia. Not all of the components of the surgical microscopy system 7 have to be arranged together with the surgical microscope 73 thereof in a room, for example.

The database 5 can be a database system comprising a plurality of hardware and software modules, which can be arranged in a distributed manner. By way of example, each surgical microscopy system 7 can comprise a software module of the database system which runs on the hardware of the surgical microscopy system and enables the interaction of the surgical microscopy system 7 with the database system 5. The data sets can be stored in data memories of the database system which are arranged at locations which differ from the locations at which the surgical microscopes of the surgical microscopy systems 7 are arranged.

During the operation of the plurality of surgical microscopy systems 7, as described below, annotated data are acquired, which are stored in a database 9 for annotated data. In a step 11, the annotated data that have been stored in the database 9 for annotated data are analysed in order, on the basis of the analysis, to create a classifier 13, which is one example of a machine learning tool created on the basis of the annotated data acquired.

Figure 2:
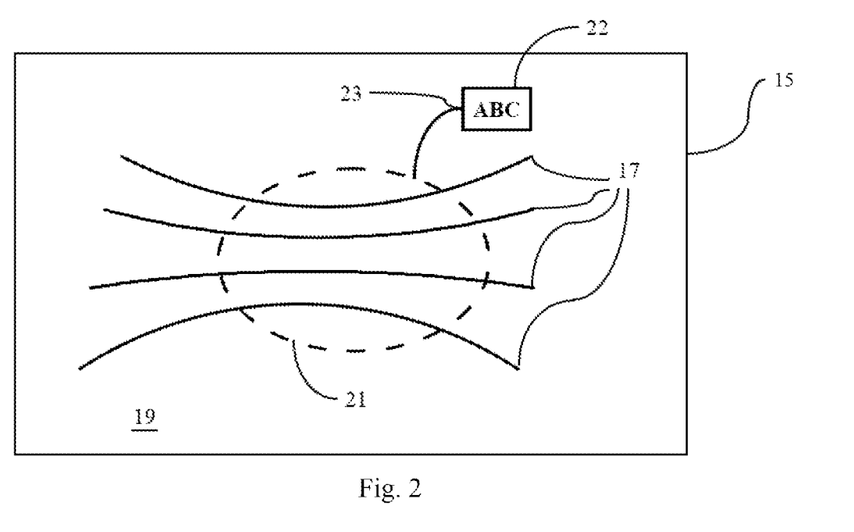
FIG. 2 shows one example of an annotated image.

FIG. 2 schematically illustrates one example of annotated data which can be acquired using a surgical microscopy system 7. FIG. 2 shows an image 15 which was recorded by the surgical microscope 73 of the surgical microscopy system 7. In the image 15, lines 17 represent structures of body tissue 19 of a patient on whom a medical intervention is performed by means of the surgical microscopy system 7. Part of the tissue 19 contains a tumour, which is recognized by the experienced user of the surgical microscopy system in the image 15. The user uses a mouse of the user interface of the surgical microscopy system 7 in order to insert a line 21 into the image 15, said line identifying a contour of the tumour in the tissue 19. In addition, the user inputs a designation 22 for the tissue identified by the line 21 as a series of letters, which is represented by "ABC" in FIG. 3 and is connected to the line 21 via a curved connecting line 23. However, it is also possible to represent the series of letters in a different way in association with the line 21. The line 21 and the series of letters 22 thus together form an annotation of data provided by the image 15. A multiplicity of such annotated data comprising different images of different patients and different annotations can subsequently be used to train a machine learning instrument which is able, in new tissue images, to recognize and highlight the regions containing tumours.

Figure 3:
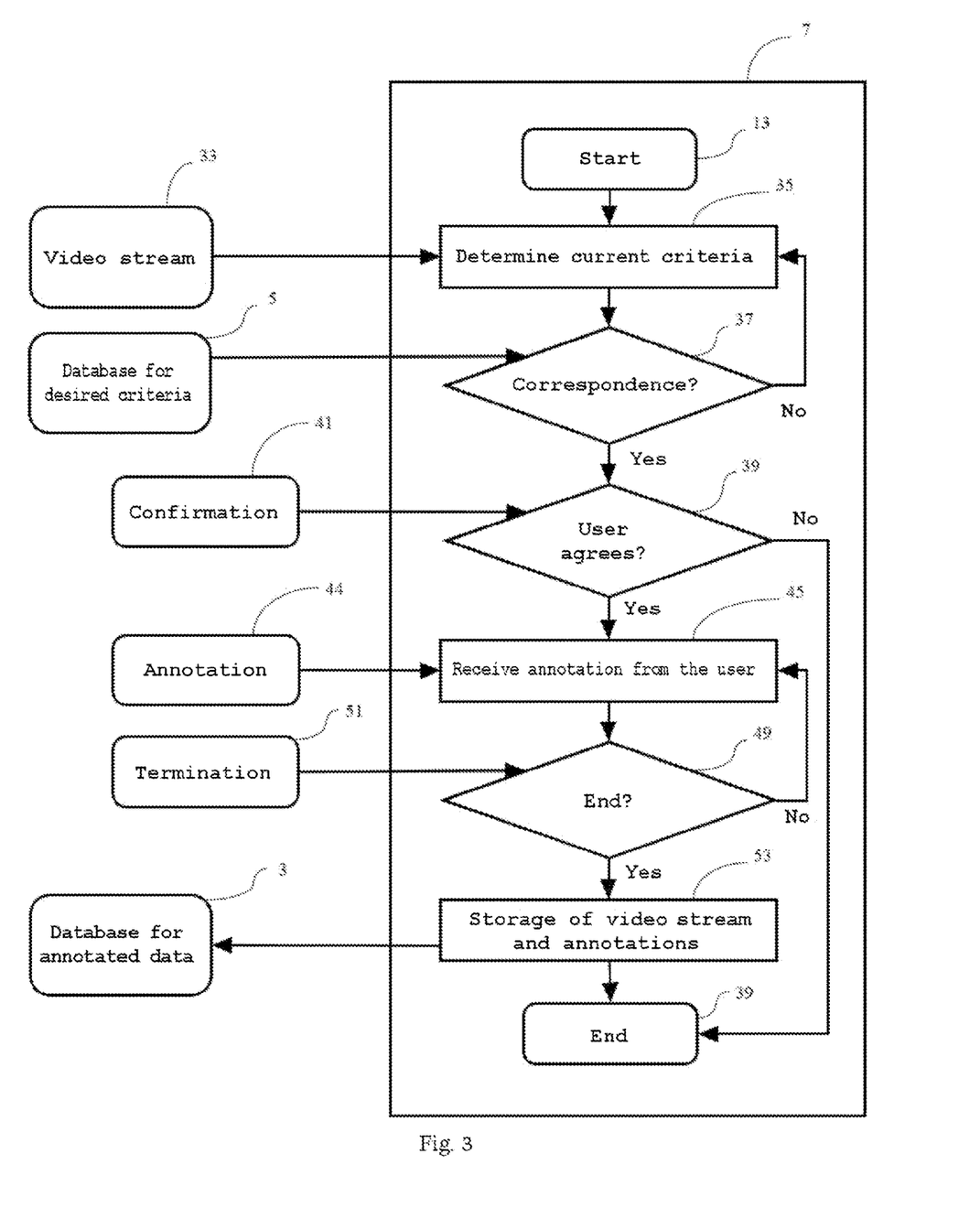
FIG. 3 shows a detail from FIG. 1.

FIG. 3 is a flow diagram for elucidating part of the method illustrated in FIG. 1, which proceeds in a surgical microscopy system 7 of the plurality of surgical microscopy systems.

The method is started in a step 31 at the beginning of an intervention which is performed on a patient and which is visualized by means of the surgical microscopy system 7. A video stream 33 generated by a camera of the surgical microscope of the surgical microscopy system is then analysed in a step 35 in order to determine current criteria. Besides the video stream 33, other sources of information, such as, for example, a database of the hospital in which the surgical microscopy system 7 is installed, can also be used for determining the current criteria in step 35.

The current criteria can furthermore comprise the instantaneous state of the surgical microscope 73. Said state can be ascertained by reading sensors and comprises for example the type of illumination used, filters used in the illumination beam path and in the analysis beam path in order to capture specific types of fluorescence examinations. Furthermore, by way of example, position sensors of the stand of the surgical microscopy system can be read in order to deduce the type of the intervention currently being carried out. Furthermore, the images recorded by cameras of the surgical microscope 73 of the surgical microscopy system can be analysed in order to recognize therein for example typical types of tissue, such as blood vessels, for example, which in turn allows the type of the intervention carried out to be deduced.

In a step 37, the current criteria determined in step 35 are compared with the desired criteria stored in the database 5 for desired criteria. If sufficient correspondence is not established in step 37, step 35 is repeated in order to make a new attempt, on the basis of the video stream 33, to determine subsequently possibly other current criteria which may result in correspondence in step 37.

If sufficient correspondence is found in step 37, in a step 39 a confirmation 41 from a user of the surgical microscopy system is requested, obtained and checked. If the confirmation obtained comprises the fact that the user does not agree to annotate data, the method is ended in a step 43.

By contrast, if the user agrees to annotate data, said user is given the opportunity to do this by the provision of the suitable user interface. In a step 45, an annotation 47 can then be obtained from the user. The annotation 47 can consist, for example, of the input—illustrated in FIG. 3—of the line 21 and the series of letters 22 with respect to an image 15 of the video stream 33. A step 49 then involves checking whether the user has input a termination 51 via the user interface. If this is not the case, further annotations 47 with respect to further images 15 of the video stream 33 are obtained in step 45. If the user terminates the further input of annotations 47 in step 49, a step 53 involves storing the annotated images 15 together with the annotations 21, 22 or the entire video stream 33 together with the annotations in the database 9 for annotated data.

As soon as enough annotated data have been stored in the database 9 for annotated data, a machine learning instrument can be trained using these data and annotations. One example of such a machine learning instrument is a classifier, the algorithm of which comprises for example a neural network, a decision tree or the like. Furthermore, a clinical hypothesis can be validated on the basis of the annotated data. Furthermore, a new classifier can also be determined on the basis of the annotated data, which new classifier can be used to determine the current criteria in step 35. The new classifier can be transferred to the surgical microscopy system in order to replace the existing classifier there.

Figure 4:
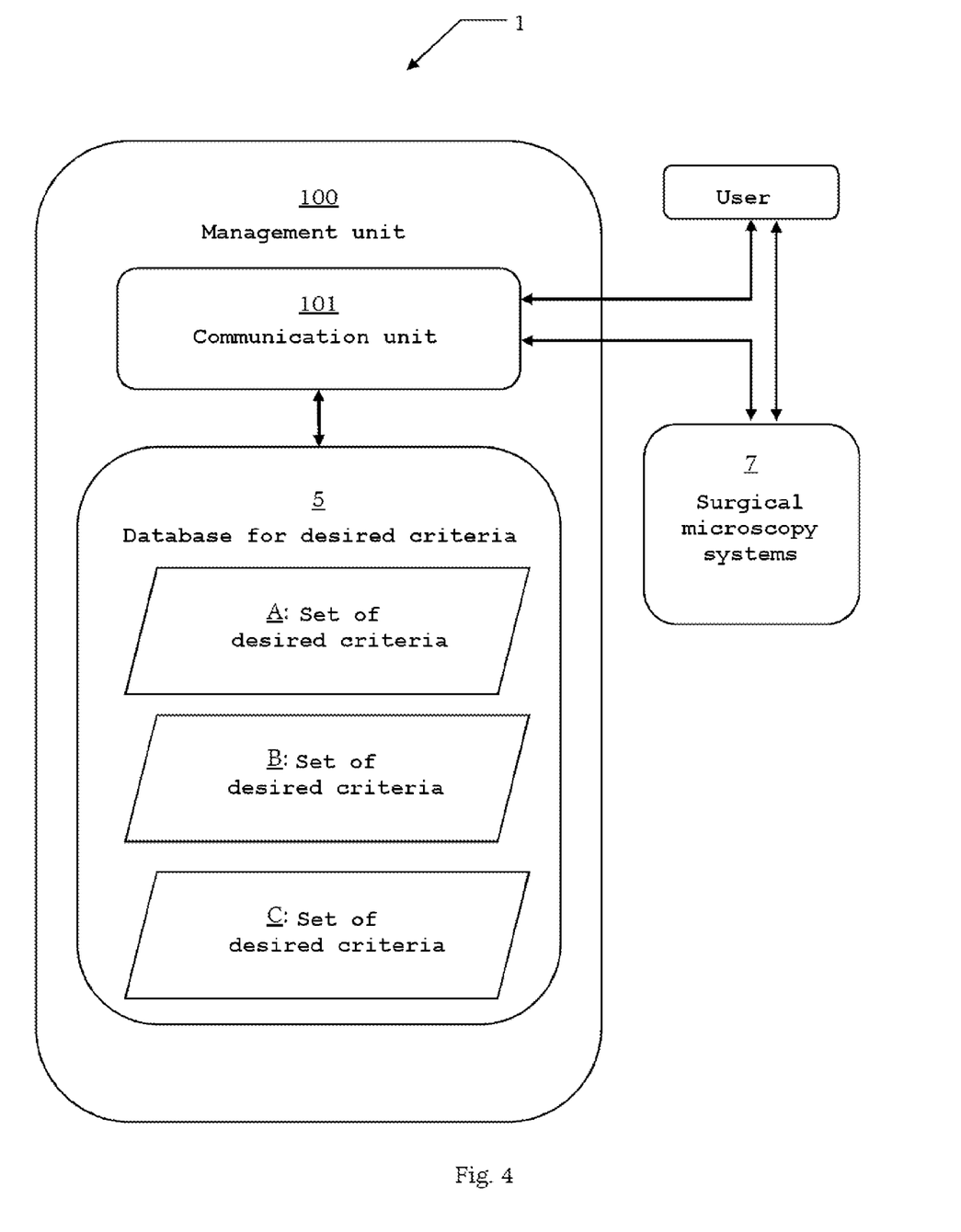
FIG. 4 shows a schematic illustration of a management unit in a system for acquiring annotated data.

FIG. 4 shows a schematic illustration of a system for acquiring annotated data. The system 1 comprises a management unit 100 and a plurality of surgical microscopy systems 7.

In particular, FIG. 4 shows a schematic illustration of the management unit 100 used to make possible the input of a new set of desired criteria and the storage and management thereof. The management unit 100 comprises for example a communication unit 101 and the database for desired criteria 5. The database can be implemented by a storage unit.

The communication unit 101 serves for communication with other components of the overall system and the user. In this regard, the communication unit 101 can comprise input and output units, for example, which allow the user to input and display the sets of desired criteria.

The database for desired criteria 5 stores the sets of desired criteria that have been input. In the example in FIG. 4, three different sets A, B and C of desired criteria have been stored in the database for desired criteria 5.

The communication unit 101 is furthermore configured to transmit one or more sets of desired criteria that have been stored in the database for desired criteria 5 to the surgical microscopy systems 7.

Figure 5:
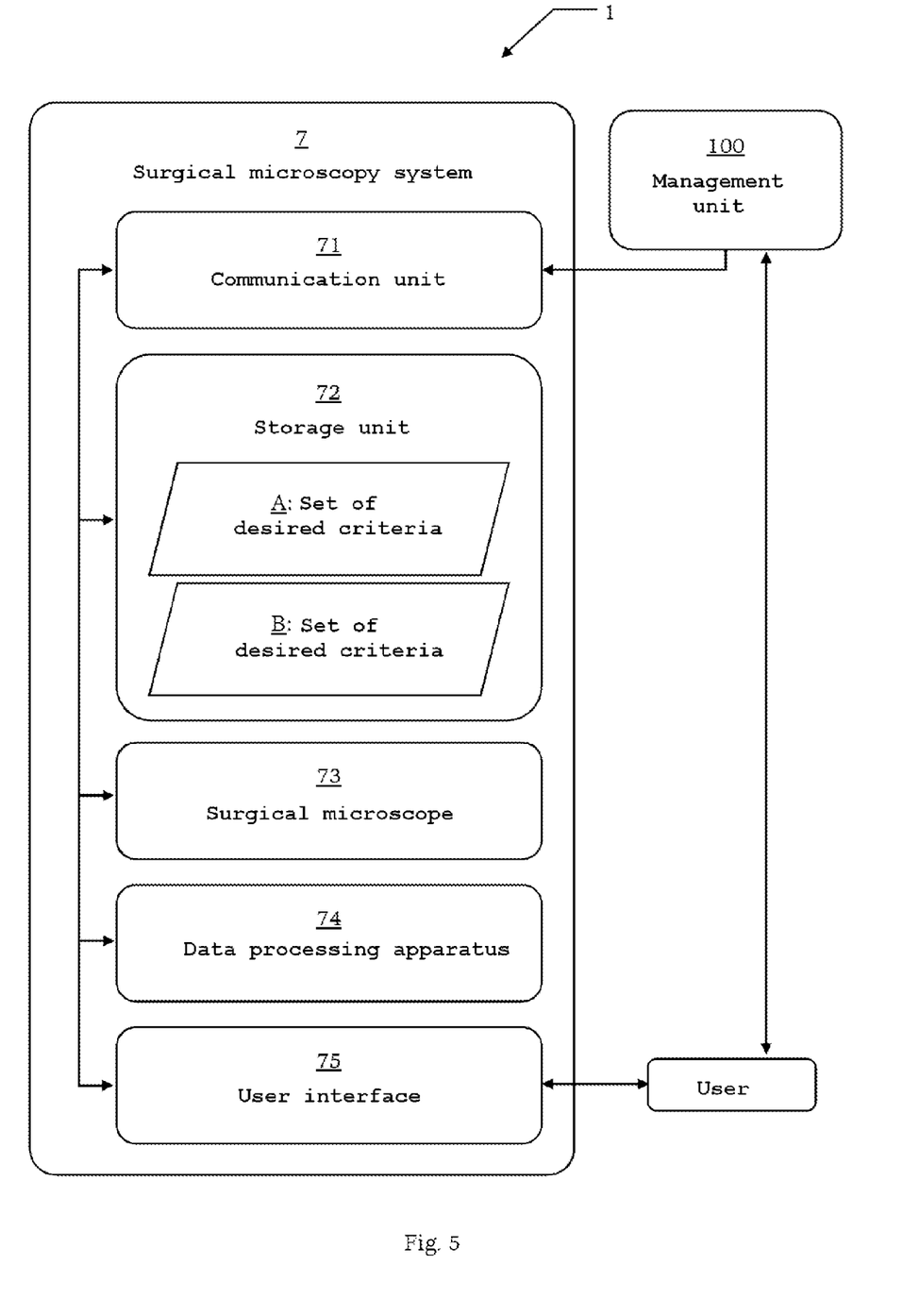
FIG. 5 shows a schematic illustration of a surgical microscopy system in the system shown in FIG. 4.

FIG. 5 shows a schematic illustration of one of the surgical microscopy systems 7 of the system 1. The surgical microscopy system comprises a communication unit 71, a storage unit 72, a surgical microscope 73, a data processing apparatus 74 and a user interface 75. The components of the surgical microscopy system 7 are connected to one another via a communication network.

The communication unit 71 serves for communication with other components of the overall system. For example, the communication unit 71 is configured to receive one or more sets of desired criteria from the management unit 100.

The storage unit 72 stores the sets of desired criteria that have been received by the communication unit 71. In the present example, not all of the sets stored in the database for desired criteria 5 were transferred to the surgical microscopy system 7, but rather only the sets A and B. The selection and management of the sets of desired criteria to be used in a surgical microscopy system 7 can for example be performed by the management unit 100 and be dependent on the constitution of the respective surgical microscopy system 7.

The surgical microscope 73 serves for recording images.

The data processing apparatus 74 is configured to carry out the method described in FIG. 2.

The user interface 75 serves for communication with the user. In this regard, the user interface 75 can comprise input and output units, for example, which make it possible to display the images recorded by the surgical microscope 73 for a user and to receive user-effected annotations and other inputs and to pass them on to the data processing apparatus 74.

Figure 6:
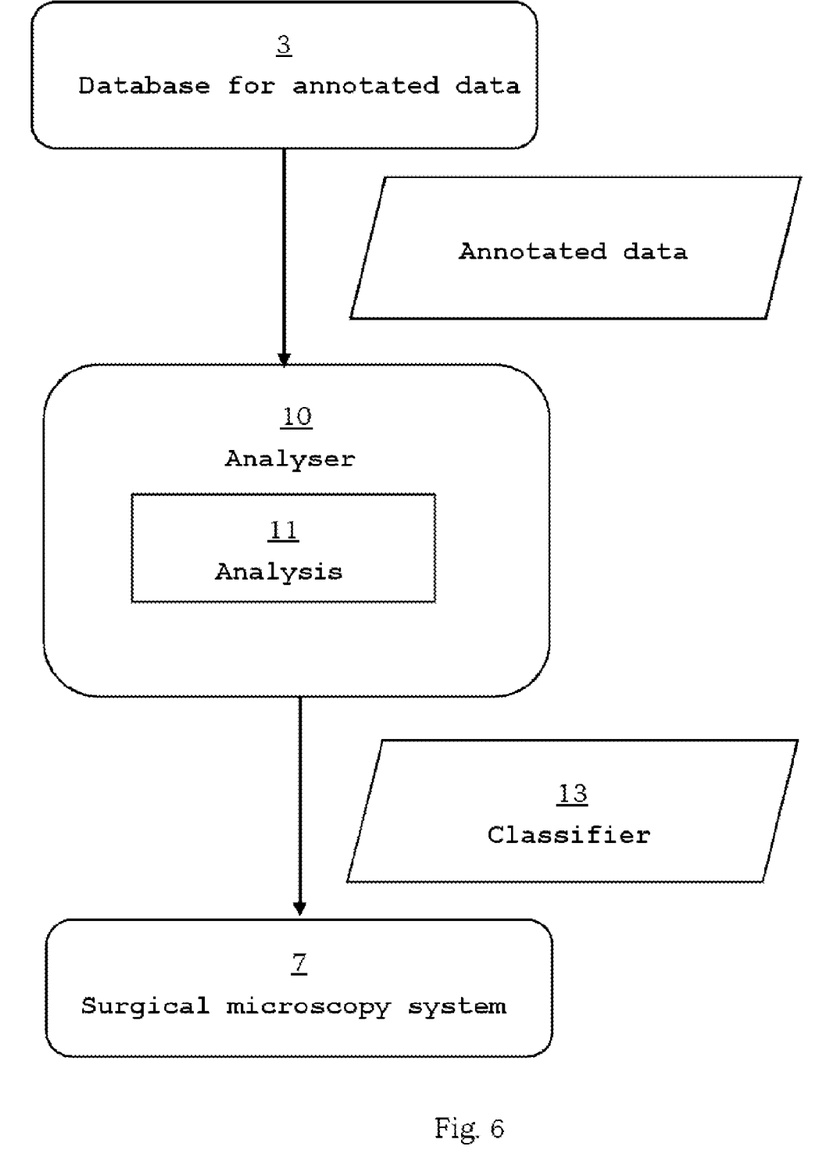
FIG. 6 shows a schematic illustration of an analyser.

FIG. 6 shows a schematic illustration of an analyser 10 configured to carry out the analysis 11. For this purpose, the analyser 10 receives annotated data from the database for annotated data 3 and analyses them. The result of the analysis 11 is an improved classifier 13, for example, which is transmitted to the surgical microscopy systems 7.

The invention claimed is:

1. A method for acquiring annotated data using a plurality of surgical microscopy systems, the method comprising the following steps performed by each of the plurality of surgical microscopy systems:
   storing at least one set of desired criteria in a storage unit of a respective surgical microscopy system;
   recording image data including at least one image using a microscope of the respective surgical microscopy system;
   determining a set of current criteria from the recorded image data;
   determining whether the determined set of current criteria sufficiently corresponds to any one of the stored at least one set of desired criteria;
   when a result of the determining whether the determined set of current criteria sufficiently corresponds to any one of the stored at least one set of desired criteria indicates that the determined set of current criteria sufficiently corresponds to any one of the stored at least one set of desired criteria, requesting a confirmation from a user of the surgical microscopy system as to whether said user would like to annotate the recorded image data; and
   when receiving a confirmation from the user in response to the requesting, receiving at least one annotation from the user using a user interface provided by the respective surgical microscopy system and storing the received at least one annotation and the recorded image data as the annotated data in a database of the respective surgical microscopy system.

2. The method according to claim 1, wherein the desired criteria specify a type of a medical intervention, an age, a sex and/or a state of health of a patient on whom the medical intervention is performed, a quality of tissue imaged in the image data, a characteristic of the user of the surgical microscopy system, a location at which the surgical microscopy system is situated, and/or a use history of the surgical microscopy system.

3. The method according to claim 1, wherein determining the set of current criteria from the recorded image data comprises requesting at least one criterion from the user, and/or obtaining at least one criterion from an information management system of a hospital in which the surgical microscopy system is situated, and/or of a company which manufactured the surgical microscopy system, and/or determining at least one criterion on the basis of the recorded images.

4. The method according to claim 1, wherein the determining indicates that the determined set of current criteria sufficiently corresponds to any one of the stored at least one set of desired criteria when an intersection of the criteria has a number of criteria that satisfies a predetermined relation with respect to a number of the criteria of the at least one set of desired criteria.

5. The method according to claim 1, wherein the annotation comprises a designation indicating a quality of tissue imaged in the image data, and/or comprises at least one graphical marking within a recorded image of the image data.

6. The method according to claim 1, wherein the database is shared by all the surgical microscopy systems.

7. The method according to claim 1, further comprising analyzing the at least one image of the stored annotated data.

8. The method according to claim 7, wherein the analyzing comprises generating a classifier with which at least one criterion of the at least one set of desired criteria is determinable on the basis of an image which is recorded by a surgical microscope and which is different from the at least one image of the stored annotated data.

9. A system for acquiring annotated data, comprising:
a management unit; and
a plurality of surgical microscopy systems;
wherein the management unit comprises:
a communication unit configured for:
obtaining at least one set of desired criteria;
transmitting the obtained at least one set of desired criteria to the plurality of surgical microscopy systems;
a database configured for:
storing the obtained at least one set of desired criteria;
wherein each of the plurality of surgical microscopy systems comprises:
a communication unit configured for:
receiving the at least one set of desired criteria transmitted by the management unit;
a storage unit configured for:
storing the at least one received set of desired criteria;
a microscope configured for:
recording image data including at least one image;
a data processing apparatus configured for:
determining a set of current criteria from the recorded image data,
determining whether the determined set of current criteria sufficiently corresponds to any one of the stored at least one set of desired criteria,
when a result of the determining indicates that the determined set of current criteria sufficiently corresponds to any one of the stored at least one set of desired criteria, requesting a confirmation from a user of the surgical microscopy system as to whether said user would like to annotate the recorded image data;
a user interface configured for:
receiving the confirmation from the user, and,
when receiving the confirmation, receiving at least one annotation from the user;

wherein the data processing apparatus is further configured for:
storing the received at least one annotation and the recorded image data as annotated data in a database of the surgical microscopy system.

10. The system according to claim 9, wherein the desired criteria specify a type of a medical intervention, an age, a sex and/or a state of health of a patient on whom the medical intervention is performed, a quality of tissue imaged in the image data, a characteristic of the user of the surgical microscopy system, a location at which the surgical microscopy system is situated, and/or a use history of the surgical microscopy system.

11. The system according to claim 9, wherein the data processing apparatus of the respective surgical microscopy system is configured, for the purpose of determining the set of current criteria from the recorded image data, to carry out requesting at least one criterion from the user, and/or obtaining at least one criterion from an information management system of a hospital in which the surgical microscopy system is situated, and/or of a company which manufactured the surgical microscopy system, and/or determining at least one criterion on the basis of the recorded images.

12. The system according to claim 9, wherein the data processing apparatus of the respective surgical microscopy system is further configured to determine that the determined set of current criteria sufficiently corresponds to any one of the stored at least one set of desired criteria when an intersection of the criteria has a number of criteria that satisfies a predetermined relation with respect to a number of the criteria of the at least one set of desired criteria.

13. The system according to claim 9, wherein the corresponding annotation comprises a designation specifying a quality of tissue imaged in the image data, and/or comprises at least one graphical marking within a recorded image of the image data.

14. The system according to claim 9,
wherein the database is shared by all the surgical microscopy systems;
wherein the data processing apparatus of the respective surgical microscopy system causes the communication unit of the respective surgical microscopy system to transfer the annotated data to the database.

15. The system according to claim 9, further comprising:
a computer-implemented analyzer configured for analyzing the at least one image of the stored annotated data.

16. The system according to claim 15, wherein the computer-implemented analyzer is configured, for the purpose of analyzing the at least one image of the stored annotated data, to carry out generating a classifier with which at least one criterion of the at least one set of desired criteria is determinable on the basis of an image which is recorded by a surgical microscope and which is different from the at least one image of the stored annotated data.

* * * * *